United States Patent [19]

Bush

[11] Patent Number: 4,587,857
[45] Date of Patent: May 13, 1986

[54] METHOD FOR MOUNTING POORLY CONSOLIDATED CORE SAMPLES

[75] Inventor: Darrell C. Bush, Colleyville, Tex.

[73] Assignee: Western Geophysical Company of America, Houston, Tex.

[21] Appl. No.: 662,279

[22] Filed: Oct. 18, 1984

[51] Int. Cl.[4] ............................................. G01N 1/28
[52] U.S. Cl. ...................................... 73/863; 73/38; 73/864.91; 53/442; 175/226
[58] Field of Search ................. 73/38, 863, 864.91; 53/442; 175/226

[56] References Cited

U.S. PATENT DOCUMENTS

| | | | |
|---|---|---|---|
| 2,662,401 | 12/1953 | Bailly | 73/38 |
| 3,199,341 | 8/1965 | Heuer et al. | 73/38 |
| 3,321,886 | 5/1967 | Griffith et al. | 53/442 |

Primary Examiner—Jerry W. Myracle
Assistant Examiner—Tom Noland
Attorney, Agent, or Firm—Kanz, Scherback & Timmons

[57] ABSTRACT

A method of mounting and confining poorly and/or unconsolidated core samples for subsequent handling and testing is disclosed. The preferred method comprises the steps of inserting a poorly consolidated core sample into a predetermined length of heat shrinkable tubing. End plugs are inserted at each end of the core sample and within the tubing. Heat is then applied to the heat shrinkable tubing and the tubing shrinks to conform to the outer circumferential surface of the core sample and the end plugs. The tubing is cut off at each end of the poorly consolidated core sample at the line of contact between the poorly consolidated core sample and each end plug. Then the poorly consolidated core sample is seated to attempt to return grains to their in situ grain to grain relationship. Suitable screens are placed against each end of the core sample. Screen caps are then attached to each end of the core sample to provide a constant pressure on the ends of the core sample. The screen caps can then be held in place with shrinkable bands or bonded to each other or tied to each other to form a very durable and useful portable laboratory sample of poorly consolidated earth.

24 Claims, 10 Drawing Figures

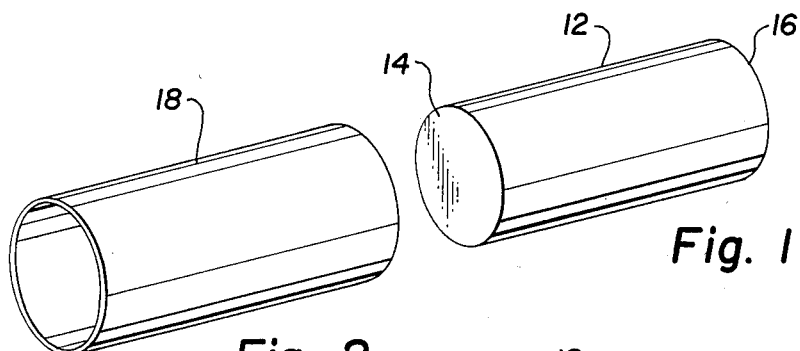
Fig. 1
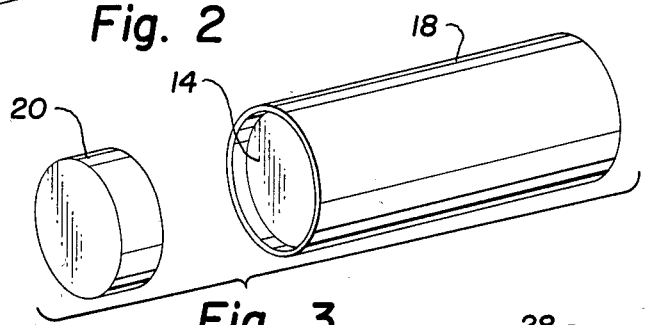
Fig. 2
Fig. 3
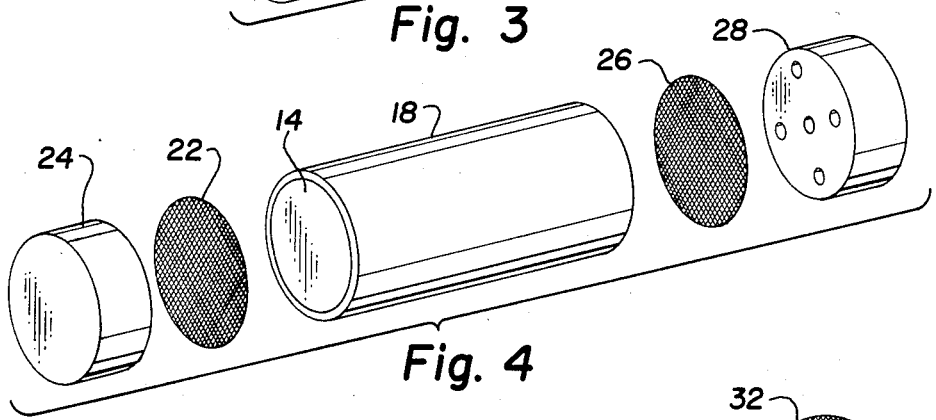
Fig. 4
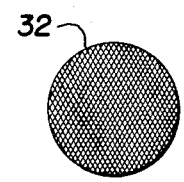
Fig. 5
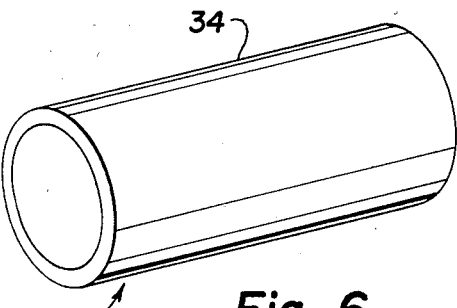
Fig. 6

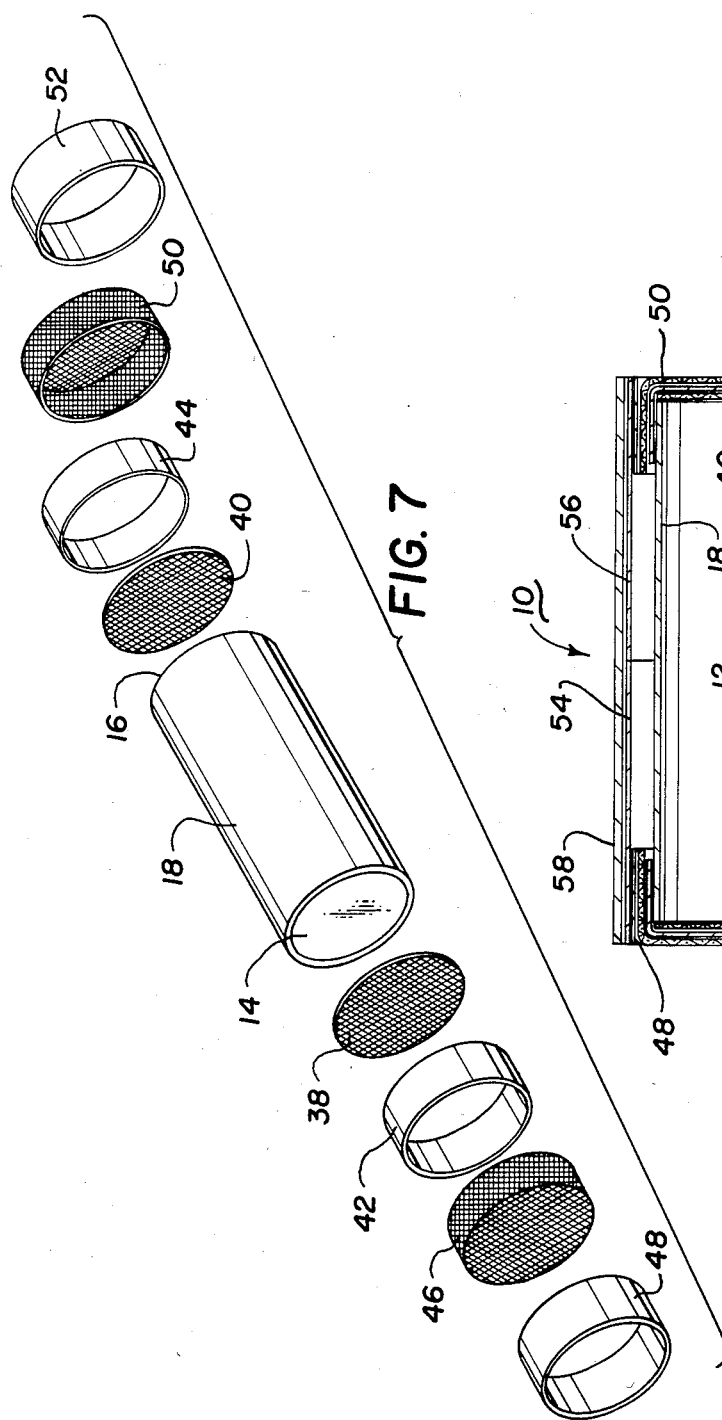

METHOD FOR MOUNTING POORLY CONSOLIDATED CORE SAMPLES

BACKGROUND OF THE INVENTION

1. Field of the Invention

The present invention relates in general to core samples removed from soft formations or loosely consolidated and unconsolidated areas or portions of the earth. More particularly, the present invention relates to methods for mounting or confining poorly consolidated and/or unconsolidated core samples for subsequent handling and testing.

2. Description of the Prior Art

It is generally the practice when drilling oil and gas wells to recover whole vertical sections of prospective geological formations at various depths in the drilling operation. This routine sampling is called coring and aids in determining the geological characteristics of the sub-structure. It is also often necessary to core drill and obtain cores of materials at construction projects and the like, as where the nature of the overburden above bedrock is to be ascertained.

In the majority of cases, the core material obtained from the core drillings is sent to a laboratory for testing. The accuracy of the analysis and testing is inversely proportional to the degree to which the integrity of the core sample is disturbed or changed as the core sample is removed from the earth, transported to the laboratory and handled at the laboratory during the testing thereof. As would be expected, greater care is needed in the handling of poorly and/or unconsolidated core samples than with consolidated core samples. Many of the prior art devices are directed to the removal of core samples from the earth. For example, U.S. Pat. No. 4,071,099 discloses a housing for receiving a conventional rubber sleeved core sample from a vertically suspended core barrel. The housing is adapted for the circulation therearound of a subfreezing mass for the freezing and solidification of the core fluids contained therethrough. Also disclosed is an elongated housing adapted for the receipt of the core while within the rubber sleeve and including means for introducing a casting medium substantially around and longitudinally along the core. Means are included for shielding an arcuate longitudinal portion of the core from the casting medium to facilitate access to the partially encased core.

U.S. Pat. No. 4,156,469 discloses a drilling system for obtaining cores of unconsolidated material by using an apparatus which permits the core barrel to remain stationary while the auger rotates. The apparatus further includes means for fitting a friction reducing sleeve of woven nylon about the core as the drilling occurs and thus permit the core to freely slide upwardly into the core barrel within the sleeve.

U.S. Pat. No. 4,371,045 discloses apparatus for removing unstable cores from the earth which includes apparatus operatively connected to the top of the drill pipe which allows the core barrel to be positioned within a chilling vessel and a cryogenic fluid to flow through the chilling vessel to stabilize the core sample before the core barrel is removed from the top of the drill pipe.

The present invention as claimed is intended to provide a solution to various prior art deficiencies which include mountings which are not suitable for allowing resistivity measurements on the poorly consolidated or unconsolidated core samples. Prior art mountings do not provide adequate viewing of the core sample to allow detection of cracks or other textural anomalies in the core sample. Some prior art mountings do not provide adequate confinement of the core sample to adequately assure the physical integrity of the core samples during handling and testing and thereby do not minimize alteration of the characteristics of the physical structure of the core sample.

SUMMARY OF THE INVENTION

The present invention provides a method of mounting and confining poorly consolidated and/or unconsolidated core samples for subsequent handling and testing. The preferred method comprises the steps of inserting a poorly consolidated core sample into a predetermined length of heat-shrinkable tubing which is slightly longer than the core sample. End plugs are inserted at each end of the core sample and within the tubing. Heat is then applied to the heat-shrinkable tubing and the tubing shrinks to conform to the outer circumferential surface of the core sample and the end plugs. The tubing is cut off at each end of the poorly consolidated core sample at the line of contact between the poorly consolidated core sample and each end plug. The poorly consolidated core sample is then frozen while positioned within the tubing. While frozen, each end of the poorly consolidated core sample along with the tubing is cut off flat and at right angles to the vertical axis of the poorly consolidated core sample. The poorly consolidated core sample is then thawed. Then the poorly consolidated core sample is seated to provide a mounted core sample. The seating step includes placing a first screen of predetermined mesh size against a first end of the poorly consolidated core sample and then placing a solid seating plug against the first screen with a force such that a portion of the solid seating plug is within the interior volume of the tubing. A second screen of a second predetermined mesh size is placed against the second and opposite end of the poorly consolidated core sample and then a seating plug with a predetermined number of passageways therethrough is placed against the second screen with a force such that a portion of the seating plug is within the interior volume of the tubing. The poorly consolidated core sample is then loaded hydrostatically in a manner to sufficiently seat the poorly consolidated core sample to attempt to return the laboratory sample grains to their in situ grain to grain relationship. Suitable screens are placed against the sample ends to permit free flow of test fluids through the sample with minimal grain loss. Screen caps are attached and cover each end of the sample to provide a mounted core sample which may be handled like a consolidated sample.

Among the advantages offered by the present invention is a resulting mounted core sample of a poorly consolidated core sample which is suitable for resistivity measurements. The mounted sample may be viewed between testing stages to detect cracks or other textural anomalies that exist or may develop during the testing. The resulting sample conforms more closely to a right cylinder with straight sides and uniform area than the popular lead sleeve mountings. The resulting mounted sample allows new screens to be added and the ends may be squared off at any time compatible with tests in progress without removing side support from the sample. There is less embedment of the shrinkable tubing into the outer exposed pores of the sample for tests at greater than 2500 psi net confining pressure than with the popular lead sleeve mountings. The present invention eliminates unwanted dead space along the length of the sample more reliably than the popular lead sleeve mountings. The present mounting maintains a slight confining pressure on the mounted sample at all times. The present 400 to 10,000 psi confining pressure embodiment does not require seating the sample at a higher than test confining pressure, as does the popular lead sleeve mounting which must be seated at about 1000 psi. The screen caps and methods used to secure them in place provide a more versatile test sample than prior art.

Examples of the more important features and advantages of this invention have thus been summarized rather broadly in order that the detailed description thereof that follows may be better appreciated. There are, of course, additional features of the invention that will be described hereinafter and which will also form the subject of the claims appended hereto. Other features of the present invention will become apparent with reference to the following detailed description of a presently preferred embodiment thereof in connection with the accompanying drawing, wherein like reference numerals have been applied to like elements.

BRIEF DESCRIPTION OF THE DRAWING

FIG. 1 is a simplified perspective view of a poorly consolidated core sample to be mounted according to the present invention;

FIG. 2 is a simplified perspective view of a first tubing component to be used in the mounting according to the present invention;

FIG. 3 is a simplified perspective view of the poorly consolidated core sample in mounting relationship with the first tubing component;

FIG. 4 is a simplified perspective view of additional components which may be used in the mounting according to the present invention;

FIG. 5 is a simplified perspective view of an additional component which may be used in the mounting according to the present invention;

FIG. 6 is a simplified perspective view of an additional tubing component used in the mounting according to the present invention;

FIG. 7 is a simplified perspective view of additional components used in the mounting according to the present invention;

FIG. 8 is a simplified cross sectional view of a poorly consolidated core sample as mounted according to the present invention;

DESCRIPTION OF THE PREFERRED EMBODIMENT

Figure 9:
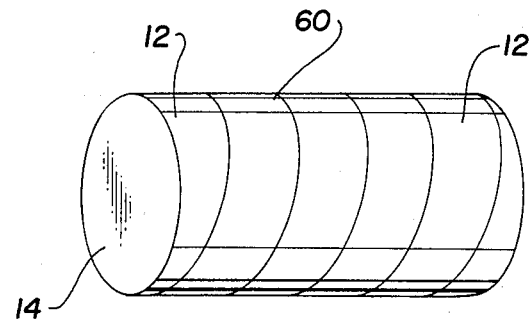
FIG. 9 is a simplified perspective view of a poorly consolidated core sample after the first step of an alternate embodiment of the present invention.

Referring now to the drawing, the mounted core sample prepared by the present preferred inventive method is generally referred to by reference numeral 10 and is depicted in FIG. 8. Various steps are performed in preparing the mounted core sample 10 with the initial step being the obtaining of the poorly consolidated core sample 12 of FIG. 1. Poorly consolidated core sample 12 is obtained by drilling into a previously obtained core from a well bore by utilizing liquid nitrogen and a diamond bit so that the poorly consolidated core sample 12 is obtained in a frozen state. Also, the poorly consolidated core sample 12 may be obtained by punching an unfrozen, poorly consolidated core from a previously obtained core from a well bore in the conventional manner using a special R & D punch. Whichever method is used, the core sample must contain enough water to be consolidated after the core sample is frozen. The first end 14 and the second end 16 of the frozen core sample may be squared off by utilizing a diamond saw, preferably cooled with liquid nitrogen. In the preferred embodiment, the poorly consolidated core sample 12 is $\frac{7}{8}$ inch in diameter and between two to three inches in length. Poorly consolidated core samples 12 which are extremely compressible may require punching or drilling with a one-inch diameter tool to obtain a $\frac{7}{8}$ inch diameter sample after seating.

The poorly consolidated core sample 12 is inserted into a first cylindrical shaped, heat shrinkable tubing 18 of predetermined length and diameter as shown in FIG. 2. In the preferred embodiment, the heat shrinkable tubing comprises a $\frac{7}{8}$ inch diameter (when shrunk) approximately four inch long section (or a section slightly longer than sample length) of FEP Teflon shrink tubing. With reference to FIG. 3, a $\frac{7}{8}$-inch diameter end plug 20 (only one shown) is inserted within the heat shrinkable tubing 18 and against the first end 14 of the poorly consolidated core sample 12 while another $\frac{7}{8}$ inch diameter end plug 20 is inserted within the heat shrinkable tubing 18 and against the second end 16 of the poorly consolidated core sample 12. Heat is then applied to the heat shrinkable tubing 18 to cause the heat shrinkable tubing 18 to shrink and conform uniformly to the outer circumferential surface of the frozen poorly consolidated core sample 12 to eliminate diameter nonconformance between the core sample 12 and the heat shrinkable tubing 18. The end plugs 20 are used to prevent the heat shrinkable tubing 18 from necking down over the first and second ends 14 and 16 of the core sample 12. Next, the end plugs 20 are removed by cutting the heat shrinkable tubing 18 off at the line of contact between the first end 14 and end plug 20 and at the line of contact between the second end 16 and end plug 20.

At this time, the poorly consolidated core sample 12 and the heat shrinkable tubing 18 are frozen and the first end 14 and the second end 16 are sawed off at right angles to the axis of the core sample 12. This operation removes any drilling mud and/or disturbed ends of the core sample 12. A core sample tube holder is used during this operation to prevent any damage to the core sample 12 during the sawing step. The core sample 12 is then allowed to thaw. In the preferred embodiment, the resulting trimmed core sample should be a right cylinder which is from one to two inches in length. Longer core samples may not fit all conventional core holders used during the seating of the core sample 12 and shorter core samples may allow bypassing of fluid flow or electrical short circuits during later testing of the mounted core sample 10.

The core sample 12 is then seated. With reference to FIG. 4, the seating procedure begins by inserting a first screen 22 against the first end 14 of core sample 12. In the preferred embodiment, first screen 22 comprises an 18 mesh screen which is $\frac{7}{8}$ inch in diameter. A solid seating plug 24 is then inserted against first screen 22 within heat shrinkable tubing 18. With a minimal amount of manual force against solid seating plug 24, core sample 12 will compress a sufficient amount to allow a small amount of the solid seating plug 24 to move within the heat shrinkable tubing 18 a sufficient depth to remain therein. If the solid seating plug 24 does not move within the heat shrinkable tubing 18 a sufficient amount, then the solid seating plug 24 may be held in place by Teflon thread tape placed across plug 24 and against the sides of the heat shrinkable tubing 18. A second screen 26 is inserted against the second end 16 of core sample 12. In the preferred embodiment, second screen 26 comprises an 18 mesh screen which is $\frac{7}{8}$ inch in diameter. A seating plug 28 with a predetermined number of passageways therethrough, in an axial direction, is then inserted against second screen 26 within heat-shrinkable tubing 18. In one preferred embodiment, the seating plug 28 had five passageways therethrough which allowed displaced fluids in the poorly consolidated core sample 12 to pass freely from the sample. With a minimal amount of manual force against seating plug 28, core sample 12 will compress a sufficient amount to allow a small amount of seating plug 28 to move within and remain within the heat shrinkable tubing 18. If this does not occur, then seating plug 28 may be held in place by Teflon thread tape. If particles of the core sample 12 flow out of the core sample 12 during the seating thereof, a first alternate screen 32 comprising a 325 mesh screen which is $\frac{7}{8}$ inch in diameter may be inserted between second screen 26 and seating plug 28. In addition, if necessary, another first screen 26 may be inserted between first alternate screen 32 and seating plug 28.

The poorly consolidated core sample 12 with the heat shrinkable tubing 18, various screens and seating plugs are inserted, as a unit, into a one-inch inside diameter, neoprene sleeve 34 having a wall thickness of $\frac{3}{8}$ inch. This resulting unit 36 is then loaded into a hydrostatic core holder with one-inch end butts. Solid seating plug 24 and seating plug 28 must be within the inside diameter of the heat shrinkable tubing 18 to avoid buckling the heat shrinkable tubing 18 along the length of the poorly consolidated core sample 12 during the further seating of the core sample 12. The resulting unit 36 in the hydrostatic core holder is then loaded hydrostatically in a manner to sufficiently seat the core sample 12 such as, 0.25 to 0.5 psi per foot of sample depth. Pressure is applied slowly to the core sample 12 and the core sample 12 is left under stress for at least fifteen minutes. The core sample 12 should be seated at as much or more net confining pressure as will be used in subsequent tests of the mounted core sample 10. The confining pressure is vented slowly from the hydrostatic core holder and the resulting unit 36 is removed from the hydrostatic core holder. The solid seating plug 24 and the seating plug 28 are removed from the resulting unit 36. Any alternate screens, if used, are also removed together with the first screen 22 and the second screen 26 from the resulting unit 36 unless the first screen 22 and/or the second screen 26 are completely embedded into the core sample 12 during the seating step. The core sample 12 is then frozen and the heat shrinkable tubing 18 is cut off flush at each end of the core sample 12.

With reference to FIG. 7, a third screen 38 is inserted against the first end 14 of core sample 12. In the preferred embodiment, third screen 38 comprises a 325 mesh screen which is $\frac{7}{8}$ inch in diameter. A fourth screen 40 is inserted against the second end 16 of core sample 12. In the preferred embodiment, fourth screen 40 comprises a 325 mesh screen which is $\frac{7}{8}$ inch in diameter. One wrap of Teflon tape 42 is positioned around the end of the heat shrinkable tubing 18 near the first end 14 such that the Teflon tape 42 laps over the end of core sample 12 and contacts the third screen 38 and holds said third screen 38 in position against core sample 12 and prevents or minimizes grain loss. Additional wraps of Teflon tape can, in the preferred embodiment, be used if needed to provide a better fit between the subsequently installed screen end caps and the sample. Teflon tape 42 is $\frac{1}{2}$-inch in width. One wrap of Teflon tape 44 is positioned around the end of the heat shrinkable tubing 18 near the second end 16 and overlaps the edge of fourth screen 40 in the same manner as Teflon tape 42 was positioned with respect to third screen 38 and the end of core sample 12. In the preferred embodiment, Teflon tape 44 is $\frac{1}{2}$-inch in width.

The first end 14 of the core sample 12 is then inserted into a first preformed screen end cap 46. In the preferred embodiment, first screen end cap 46 is formed of 60 mesh screen. A paper label with core sample identification data in India ink may be placed against the side of first screen end cap 46. A band 48 of heat shrinkable tubing is then placed over the first screen end cap 46 such that the outer end of band 48 is flush with the outer end of the first screen end cap 46. In the preferred embodiment, band 48 is $\frac{3}{8}$ inch in width.

The second end 16 of the core sample 12 is then inserted into a second preformed screen end cap 50. In the preferred embodiment, second screen end cap 50 is formed of 60 mesh screen. A band 52 of heat shrinkable tubing is then placed over the second screen end cap 50 such that the outer end of band 52 is flush with the outer end of the second screen end cap 50. In the preferred embodiment, band 52 is $\frac{3}{8}$ inch in width.

The thus assembled sample and mounting elements are placed in a device which causes a pressure of about eight psi to be applied to the ends of the core sample 12. The value of eight psi was chosen to approximately equal the pressure exerted on the cylindrical surface of the core sample 12 by the heat shrinkable tubing 18 after it has had heat applied to it. Thus, equal pressure is applied to all surfaces of the core sample 12.

Heat is then applied to bands 48 and 52 to shrink bands 48 and 52 down onto the first and second screen end caps 46 and 50. The sample is now suitably mounted for saturation tests, permeability tests, porosity tests, and resistivity tests.

The screen end caps can be bonded together and their porous sides made solid for more sophisticated tests. The Teflon band covering the screen end cap sides is removed before proceeding with the following low temperature (less than 160° F.) mounting. The mounted sample is placed in the device that places about 8 psi on the sample ends before the Teflon bands are removed. A first section 54 of special low temperature meltable soft sleeve material, which is equal in length to one-half the length of the core sample 12, is then slipped over and positioned on the left half of core sample 12. A second section 56 of the special low temperature meltable soft sleeve material, which is equal in length to one-half the length of the core sample 12, is then slipped over and positioned on the right half of core sample 12. The special low temperature meltable soft sleeve material used in the present embodiment is soft thermoplastic ML-326 meltliner tubing available under the trademark INSULTITE. An identification label may then be applied to either of the sections of special low temperature meltable soft sleeve material. An outside section 58 of heat shrinkable tubing, which is equal in length to the core sample 12, is then slipped over, in a covering position, the first and second sections 54 and 56 of the special low temperature meltable soft sleeve material. In the preferred embodiment, outside section 58 comprises FEP Teflon shrinkable tubing of one inch inside diameter with about 0.015- to 0.018-inch wall thickness. Heat is then applied to the outside section 58 to shrink the outside section 58 to fit the sample and to also melt the first and second sections 54 and 56 so the material will fill in any dead space along the sides of first and second screen end caps 46 and 50 to form a complete encapsulation of the core sample 12 with the first and second screen end caps 46 and 50 being bonded to each other by and through the first and second sections 54 and 56 of the special low temperature meltable soft sleeve material. The application of the heat is maintained to further shrink the outside section 58 and to melt the first and second sections 54 and 56 near the ends of core sample 12 until the outside section 58 necks down over the first and second screen end caps 46 and 50 at each end of the core sample 12. The INSULTITE melts sufficiently at about 220° F. The sample can be frozen or made moist before applying heat to minimize damage to hydratable minerals such as clays. The mounted core sample 10 is allowed to cool in a vertical position and then the outside section 58 is trimmed together with the first and second sections 54 and 56 flush with the outer surface of first and second screen end caps 46 and 50. The mounted core sample 10 is now essentially as durable as a consolidated sample at less than 160° F. and is suitable for testing at no less than 2500 psi net confining pressure.

An alternate embodiment of the mounted core sample 10 is provided for more sophisticated and demanding special core analysis tests. These tests require removal of the dead air space on the sides of the screen end caps and it is desirable to secure the screen end caps to each other to help maintain a slight pressure on the mounted core sample 10 when the mounted core sample 10 is outside the core holder. The material used for these two purposes is required to withstand hot (less than 350° F.) solvents used in cleaning the hydrocarbons and salts from the samples. Special Nylon tubing (such as Nylon 11, available under the trademark BESNO from Rilsan Industrial Inc.) is preferred for this purpose. The sample is held in a device with 8 psi of pressure on the screen end caps. The Teflon collars 48 and 52 used above can be cut off, and two close fitting, ½ sample lengths, of Nylon tubing can be slipped over the screen end caps on each end of the sample instead of the special low temperature meltable material described above. An identification can be applied to the first Teflon sleeve before placing the Nylon 11 tubing over the screen end caps and sample. An outside section 58 of heat shrinkable tubing is applied as above to press the underlying melting Nylon 11 tubing into the sides of the screen end caps to remove dead air space and fit the Nylon 11 tubing to the surface of the sample and to melt the first and second sections 54 and 56 together to form a complete encapsulation of the core sample 12 with the first and second screen end caps 46 and 50 being bonded to each other by and through the first and second sections 54 and 56 of Nylon 11 sleeve material. The Nylon melts sufficiently at about 400° F. The sample can be frozen or made moist before applying heat to minimize damage to hydratable minerals such as clays. The sample can be cooled after melting the Nylon 11 sufficiently and the outside section 58 of heat shrinkable Teflon tubing can be removed, if desired, and discarded to reduce the thickness of plastics covering the sample. However, the outside shrinkable Teflon sleeve adds durability to the mounting and provides additional compressional stress on the sample if not removed. The first and second sections 54 and 56 and outside section 58 are trimmed flush with the outer flat face surface of first and second screen end caps 46 and 50. The mounted core sample 10 is now essentially as durable as a consolidated sample at less than 350° F. and is suitable for testing at no less than 2500 psi net confining pressure. A single wrap of ¼-inch wide Teflon thread tape can be placed near the middle of the sample length and between the Nylon and Teflon sleeves during the mounting procedure to insure against the possible occurrence of test fluid bypassing or electrical short circuits.

An alternate embodiment of the mounted core sample 10 is provided for testing from 400 to 10,000 psi net confining pressure at less than 400° F. With reference to FIG. 9, the poorly consolidated core sample 12 is first wrapped with thin soft Teflon thread tape 60 (to prevent test fluid from bypassing the sample at 400 to 2500 psi net confining pressure). The thread tape is transparent enough when saturated with refined oils or oil solvents to allow the sample textures to be seen through the tape. Refined oils and oil solvents are commonly used in restored state core analysis. In the preferred embodiment, the thin soft tape 60 comprises a soft tape of about 0.003 inch in thickness. The core sample 12 with the thin soft tape 60 thereon is then inserted into a cylindrical shaped, heat shrinkable tubing 18 of predetermined length and diameter as shown in FIG. 2. In the preferred embodiment, the heat shrinkable tubing 18 comprises a ⅞-inch diameter (when shrunk) approximately four inches long section or slightly more than sample length of FEP Teflon shrink tubing. The remaining steps to be performed to provide a mounted core sample 10 for testing from 400 to 10,000 psi net confining pressure are the same steps depicted in FIGS. 3 through 8 as previously discussed.

Another alternate embodiment is to use a Nylon 11 film in place of the Teflon tape described above to prevent test fluid by passing the sample at 400 to 10,000 psi net confining pressure at less than 350° F. The Nylon 11 film does not require any sample porosity correction and it is transparent, but must be melted to seal against the sample to prevent bypassing. The Nylon film melts sufficiently at about 400° F. The Nylon film used covers the sample except for approximately 3/16 of an inch of the ends to allow for flow during the melting steps, so as not to get Nylon on the face of the sample. The sample can be frozen or made moist before applying heat to minimize damage to hydratable minerals such as clays. The mounting steps are the same as discussed above for Teflon thread tape.

Figure 10:
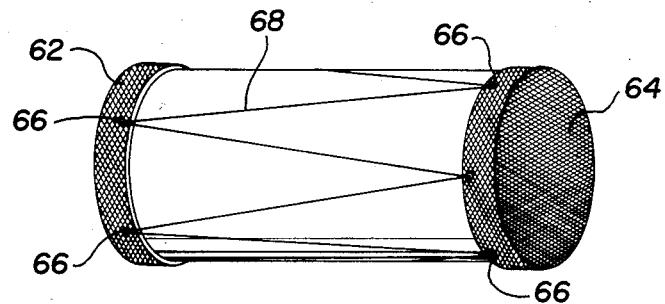
FIG. 10 is a simplified perspective view of a poorly consolidated core sample as mounted according to an alternate embodiment of the present invention.

An alternate embodiment of the mounted core sample 10 is depicted in FIG. 10 in which screen end caps 62 and 64 are provided over opposite ends of core sample 12. Apertures 66 are provided at predetermined locations around the screen end caps 62 and 64 with line or cord 68 being laced back and forth, in a manner likened to a snare drum, to place tension on the ends of the mounted core sample 10. Tests fluids are prevented from bypassing the sample by a small drop of petroleum jelly placed on each lace just before confinement in a core holder for testing.

Although the present invention has been described in conjunction with specific forms thereof, it is evident that may alternatives, modifictions and variations will be apparent to those skilled in the art in light of the foregoing disclosure. Accordingly, this description is to be construed as illustrative only and is for the purpose of teaching those skilled in the art the manner of carrying out the invention. It is understood that the forms of the invention herewith shown and described are to be taken as the presently preferred embodiment. Various changes may be made in the shape, size and arrangement of parts. For example, equivalent elements may be substituted for those illustrated and described herein, parts may be reversed, and certain features of the invention may be utilized independently of other features of the invention. It will be appreciated that various modifications, alternatives, variations, etc., may be made without departing froa the spirit and scope of the invention as defined in the appended claims.

What is claimed is:

1. A method of mounting unconsolidated or poorly consolidated core samples to provide a mounted core sample suitable ror testing at no less than 2500 psi net confining pressure, said method comprising the steps of:
providing a poorly consolidated core sample of cylindrical shape and of predetermined length and having a first end and a second end;
inserting said poorly consolidated core sample into a predetermined length of a first cylindrical shaped, heat shrinkable tubing of predetermined diameter, said predetermined length of said first cylindrical shaped, heat shrinkable tubing being at least as great in length as said poorly consolidated core sample;
placing an end plug at each of said first and second ends of said poorly consolidated core sample within said predetermined length of said first cylindrical shaped, heat shrinkable tubing;
applying heat to said first cylindrical shaped, heat shrinkable tubing to cause said first cylindrical shaped, heat shrinkable tubing to conform to the outer circumferential surface of the poorly consolidated core sample and the end plugs;
cutting said first cylindrical shaped, heat shrinkable tubing off at each of said first and second ends at the line of contact between the poorly consolidated core sample and each end plug;
placing a first screen of a first predetermined mesh size against said first end of said poorly consolidated core sample:
placing a solid seating plug against said first screen;
placing a second screen of a second predetermined mesh size against said second end of said poorly consolidated core sample;
placing a seating plug with a predetermined number of passageways therethrough against said second screen such that said predetermined number of passageways will accommodate displaced fluids in the poorly consolidated core sample; and,
loading the poorly consolidated core sample hydrostatically in a manner to sufficiently seat the poorly consolidated core sample.

2. The method of claim 1 wherein the loading step includes the steps of:
inserting said poorly consolidated core sample with said first and second screen, said solid seating plug and said seating plug into a predetermined length of a second cylindrical shaped tubing of predetermined diameter; and,
inserting said predetermined length of said second cylindrical shaped tubing into a hydrostatic core holder.

3. The method of claim 1 further including the steps of:
freezing the seated core sample;
cutting the first cylindrical shaped, heat shrinkable tubing flush to the face of said seated core sample at the first and second ends of said seated core sample;
placing a third screen of a third predetermined mesh size against the first end of said seated core sample;
placing a fourth screen of a fourth predetermined mesh size against the second end of said seated core sample;
placing a first one wrap of tape of a predetermined width around the end portion of the first end of said seated core sample such that the first one wrap of tape overlaps both the first cylindrical shaped, heat shrinkable tubing and the third screen, said first one wrap of tape to prevent grain loss around the edge of said third screen;
placing a second one wrap of tape of a predetermined width around the end portion of the second end of said seated core sample such that the second one wrap of tape overlaps both the first cylindrical shaped, heat shrinkable tubing and the fourth screen, said second one wrap of tape to prevent grain loss around the edge of said fourth screen.

4. The method of claim 3 further including the steps of:
inserting the first end of said seated core sample into a first preformed screen end cap of a fifth predetermined mesh size;
placing a third cylindrical shaped, heat shrinkable tubing of predetermined length over said first end of said seated core sample such that a first end of said third cylindrical shaped, heat shrinkable tubing is substantially flush with an outer end of said first preformed screen end cap;
applying heat to said third cylindrical shaped, heat shrinkable tubing to cause said third cylindrical shaped, heat shrinkable tubing to conform to the outer circumferential surface of said seated core sample and said first preformed screen end cap;
inserting the second end of said seated core sample into a second preformed screen end cap of a sixth predetermined mesh size;
placing a fourth cylindrical shaped, heat shrinkable tubing of predetermined length over said second end of said seated core sample such that a first end of said fourth cylindrical shaped, heat shrinkable tubing is substantially flush with an outer end of said second preformed screen end cap; and,
applying heat to said fourth cylindrical shaped, heat shrinkable tubing to cause said fourth cylindrical shaped, heat shrinkable tubing to conform to the outer circumferential surface of said seated core sample and said second preformed screen end cap.

5. The method of claim 4 further including the steps of:
removing said third cylindrical shaped, heat shrinkable tubing from said seated core sample;
removing said fourth cylindrical shaped, heat shrinkable tubing from said seated core sample;
placing a fifth cylindrical shaped, meltable sleeve tubing over said seated core sample such that a first one half of said seated core sample is covered;
placing a sixth cylindrical shaped, meltable sleeve tubing over said seated core sample such that a second one half of said seated core sample is covered;

placing a seventh cylindrical shaped, heat shrinkable tubing over said fifth and sixth cylindrical shaped, meltable sleeve tubing and said seated core sample; and, applying heat to said seventh cylindrical shaped, heat shrinkable tubing and said fifth and sixth cylindrical shaped, meltable sleeve tubing until said fifth and sixth cylindrical shaped, meltable sleeve tubing melts over the entire surface thereof and said seventh cylindrical shaped, heat shrinkable tubing necks down over said first and second preformed screen end caps.

6. The method of claim 5 wherein said meltable sleeve tubing comprises thermoplastic ML-326 Meltliner tubing.

7. The method of claim 5 wherein said meltable sleeve tubing comprises Nylon 11.

8. The method of claim 4 wherein said fifth predetermined mesh size comprises 60 mesh.

9. The method of claim 4 wherein said sixth predetermined mesh size comprises 60 mesh.

10. The method of claim 3 wherein said third predetermined mesh size comprises 325 mesh.

11. The method of claim 3 wherein said fourth predetermined mesh size comprises 325 mesh.

12. The method of claim 1 wherein said first cylindrical shaped, heat shrinkable tubing comprises FEP Teflon tubing.

13. The method of claim 1 wherein said first predetermined mesh size comprises 18 mesh.

14. The method of claim 1 wherein said second predetermined mesh size comprises 18 mesh.

15. A method of mounting unconsolidated or poorly consolidated core samples to provide a mounted core sample suitable for testing from 400 to 10,000 psi net confining pressure with substantially zero bypassing, said method comprising the steps of:

providing a poorly consolidated core sample of cylindrical shape and of predetermined length and having a first end and a second end;

wrapping the poorly consolidated core sample with a predetermined material of predetermined thickness;

inserting the poorly consolidated core sample with the predetermined material wrapped thereon into a first cylindrical shaped, heat shrinkable tubing of a length which is at least ¼ inch longer in length than the poorly consolidated core sample;

position said poorly consolidated core sample with the predetermined material wrapped thereon with the first cylindrical shaped, heat shrinkable tubing such that the tubing extends at least ⅛ inch beyond the first end and the second end of said sample;

placing an end plug at each of said first and second ends of said poorly consolidated core sample within said predetermined length of said first cylindrical shaped, heat shrinkable tubing;

applying heat to said first cylindrical shaped, heat shrinkable tubing to cause said first cylindrical shaped, heat shrinkable tubing to conform to the outer circumferential surface of the poorly consolidated core sample and the end plugs;

cutting said first cylindrical shaped, heat shrinkable tubing off at each of said first and second ends at the line of contact between the poorly consolidated core sample and each end plug;

freezing the poorly consolidated core sample;

cutting each of said first and second ends of the poorly consolidated core sample off flat and at right angles to the axis of the poorly consolidated core sample;

thawing the poorly consolidated core sample; and, seating the poorly consolidated core sample to provide a seated core sample.

16. The method of claim 15 further including the steps of:

freezing the seated core sample;

cutting the first cylindrical shaped, heat shrinkable tubing flush to the face of said seated core sample at the first and second ends of said seated core sample;

placing a third screen of a third predetermined mesh size against the first end of said seated core sample;

placing a fourth screen of a fourth predetermined mesh size against the second end of said seated core sample;

placing a first one wrap of tape of a predetermined width around the end portion of the first end of said seated core sample such that the first one wrap of tape overlaps both the first cylindrical shaped, heat shrinkable tubing and the third screen, said first one wrap of tape to prevent grain loss around the edge of said third screen; and, placing a second one wrap of tape of a predetermined width around the end portion of the second end of said seated core sample such that the second one wrap of tape overlaps both the first cylindrical shaped, heat shrinkable tubing and the fourth screen, said second one wrap of tape to prevent grain loss around the edge of said fourth screen.

17. The method of claim 16 further including the steps of:

inserting the first end of said seated core sample into a first preformed screen end cap of a fifth predetermined mesh size;

placing a third cylindrical shaped, heat shrinkable tubing of predetermined length over said first end of said seated core sample such that a first end of said third cylindrical shaped, heat shrinkable tubing is substantially flush with an outer end of said first preformed screen end cap;

applying heat to said third cylindrical shaped, heat shrinkable tubing to cause said third cylindrical shaped, heat shrinkable tubing to conform to the outer circumferential surface of said seated core sample and said first preformed screen end cap;

inserting the second end of said seated core sample into a second preformed screen end cap of a sixth predetermined mesh size;

placing a fourth cylindrical shaped, heat shrinkable tubing of predetermined length over said second end of said seated core sample such that a first end of said fourth cylindrical shaped, heat shrinkable tubing is substantially flush with an outer end of said second preformed screen end cap; and, applying heat to said fourth cylindrical shaped, heat shrinkable tubing to cause said fourth cylindrical shaped, heat shrinkable tubing to conform to the outer circumferential surface of said seated core sample and said second preformed screen end cap.

18. The method of claim 17 further including the steps of:

removing said third cylindrical shaped, heat shrinkable tubing from said seated core sample;

removing said fourth cylindrical shaped, heat shrinkable tubing from said seated core sample;

placing a fifth cylindrical shaped, soft sleeve tubing over said seated core sample such that a first one half of said seated core sample is covered;

placing a sixth cylindrical shaped, soft sleeve tubing over said seated core sample such that a second one half of said seated core sample is covered;

placing a seventh cylindrical shaped, heat shrinkable tubing over said fifth and sixth cylindrical shaped, soft sleeve tubing and said seated core sample; and, applying heat to said seventh cylindrical shaped, heat shrinkable tubing and said fifth and sixth cylindrical shaped, soft sleeve tubing until said fifth and sixth cylindrical shaped, soft sleeve tubing melts over the entire surface thereof and said seventh cylindrical shaped, heat shrinkable tubing necks down over said first and second preformed screen end caps.

19. The method of claim 15 wherein said predetermined material comprises Teflon tape.

20. The method of claim 15 wherein said predetermined material comprises Nylon 11 film.

21. A mounted core sample comprising:

a poorly consolidated core sample of cylindrical shape and of predetermined length and having a first end and a second end;

a first heat shrinkable tubing surrounding the outer circumferential surface of said poorly consolidated core sample for applying a predetermined pressure thereto;

a first preformed screen cap of a predetermined mesh size mounted on said first end of said poorly consolidated core sample, said first preformed screen cap having a predetermined portion thereof contacting the outer surface of said first heat shrinkable tubing;

a second preformed screen cap of a predetermined mesh size mounted on said second end of said poorly consolidated core sample, said second preformed screen cap having a predetermined portion thereof contacting the outer surface of said first heat shrinkable tubing; and means to secure said first and second preformed screen caps to said poorly consolidated core sample to apply and maintain a pressure to said first and second ends, said pressure being approximately equal to said predetermined pressure.

22. A mounted core sample according to claim 21 further comprising a wrapping of a selected material of a predetermined thickness in contact with the outer circumferential surface of said poorly consolidated core sample and positioned between said poorly consolidated core sample and said first heat shrinkable tubing.

23. A mounted core sample according to claim 22 wherein said means to secure includes soft sleeve tubing substantially surrounding the outer circumferential surface of said first heat shrinkable tubing and contacting said predetermined portion of said first preformed screen cap and said predetermined portion of said second preformed screen cap.

24. A mounted core sample according to claim 23 wherein said means to secure further includes a second heat shrinkable tubing surrounding the outer surface of said soft sleeve tubing.

25. A method of mounting unconsolidated or poorly consolidated core samples to provide a mounted core sample suitable for testing, said method comprising the steps of:

providing an unconsolidated or poorly consolidated core sample of cylindrical shape and of predetermined length and having a first end and a second end;

surrounding the outer circumferential surface of said unconsolidated or poorly consolidated core sample with heat shrinkable tubing;

applying heat to said heat shrinkable tubing to establish a predetermined pressure against the outer circumferential surface of said unconsolidated or poorly consolidated core sample;

placing a first preformed screen cap of a predetermined mesh size on said first end of said unconsolidated or poorly consolidated core sample, said first preformed screen cap having a predetermined portion thereof contacting the outer surface of said heat shrinkable tubing;

placing a second preformed screen cap of a predetermined mesh size on said second end of said unconsolidated or poorly consolidated core sample, said second preformed screen cap having a predetermined portion thereof contacting the outer surface of said heat shrinkable tubing; and securing said first and second preformed screen caps to said unconsolidated or poorly consolidated core sample to apply and maintain a pressure to said first and second ends, said pressure being approximately equal to said predetermined pressure.

* * * * *